United States Patent [19]

Mostarda et al.

[11] Patent Number: 5,046,612
[45] Date of Patent: Sep. 10, 1991

[54] SAFETY APPARATUS FOR EXTRACTING HYPODERMIC NEEDLES FROM THE RESPECTIVE SYRINGE

[76] Inventors: Jorge F. Mostarda; Ricardo A. Brizuela, both of Calle 23 No. 1949 (1900), La Plata, Prov. of Buenos Aires, Argentina

[21] Appl. No.: 530,599

[22] Filed: May 30, 1990

[30] Foreign Application Priority Data

Jun. 1, 1989 [AR] Argentina .................. 314.058

[51] Int. Cl.⁵ ........................................ B65D 85/64
[52] U.S. Cl. .................... 206/365; 206/366; 604/192; 604/263
[58] Field of Search ........... 206/364, 365, 366, 63.5; 604/192, 198, 263

[56] References Cited

U.S. PATENT DOCUMENTS

| | | | |
|---|---|---|---|
| 4,315,592 | 2/1982 | Smith | 206/366 X |
| 4,643,722 | 2/1987 | Smith, Jr. | 206/365 X |
| 4,664,259 | 5/1987 | Landis | 206/365 |
| 4,917,243 | 4/1990 | Abrams et al. | 206/365 |
| 4,927,076 | 5/1990 | Simpson | 206/366 X |

FOREIGN PATENT DOCUMENTS

| | | | |
|---|---|---|---|
| 294916 | 12/1988 | European Pat. Off. | 604/192 |
| 2620341 | 3/1989 | France | 604/263 |

Primary Examiner—William I. Price

[57] ABSTRACT

A receptacle for extracting hypodermic needles from syringes. The extracted needles are held within the receptacle which has a notched surface that converges to a longitudinal slot. The needle enters the receptacle sideways through the slot. Retention means maintain a syringe and needle in position so that separation of the needle is safely effected.

8 Claims, 1 Drawing Sheet

SAFETY APPARATUS FOR EXTRACTING HYPODERMIC NEEDLES FROM THE RESPECTIVE SYRINGE

FIELD OF THE INVENTION

The present invention relates to a safety apparatus for extracting hypodermic needles from the respective syringe, constituting an exceedingly practical element in the use of such needles, without the danger of accidents for the user.

BACKGROUND OF THE INVENTION

The manipulation of hypodermic syringes, particularly of those already used, entails a risk, bearing in mind the nature thereof and their condition of sharpened elements, which are susceptible of easily penetrating or injuring animal tissues.

Therefore, in manipulating said instruments, physicians and nurses, to reduce the risk of injuring themselves or contaminating the needles, try to withdraw the hood or protecting sheath only at the moment of use. Said protecting sheath is a lengthened receptacle into which said needle is introduced through one of the open ends of the sheath, which is normally, closed at the other end.

Although the sheath offers acceptable safety during manipulation of the needle until its use on the patient, the sheath does not give any safety after the moment in which it is withdrawn, because the sheath has a very small diameter. It is very easy to fail in the attempt of re-inserting the needle in the sheath and the needle may injure the person effecting the maneuver, with the imaginable risk of disease transmissions, since the needle has been already used and is already contaminated.

For this reason, it is now recommended to avoid making the re-sheathing maneuver, and it is insisted that a rigid and strong casing be used as a receptacle for contaminated needles.

However, in many cases, the assembly of needle and syringe cannot be discarded inside said casing, either because the casing is not at hand, or because it is imperative to extract the needle from the syringe. For example, in blood extractions, for passing the blood to the test tubes, the needle should not be maintained inserted, as the passage of blood from the syringe through the needle produces hemolysis, i.e., destruction of the red cells, with the consequence that the blood sample is unusable.

It is in this moment when the maneuver required to withdraw the needle offers the above cited dangers of contagion by wounds or contamination by contact with the blood.

In order to avoid such risks, several apparatuses have been conceived for separating the needle from the syringe. The U.S. Pat. No. 4,375,849, of Sage Products, Inc., granted Mar. 8, 1983, protects an apparatus of cylindrical configuration which has in an end a key-shaped orifice, with the opposite end being closed. For the operation of said apparatus, the cylinder is taken with one hand and, with the opposed hand, the syringe with the mounted needle is taken, and the needle is introduced in the widest portion of the orifice. Then the needle is run to the narrowest portion of said orifice with the purpose of locking the base of the needle. When pulling, the needle is dislodged and the needle is definitely housed inside the cylinder. The operation of this apparatus brings out the risk of opposing the point of the contaminated needle to the hand holding the apparatus, since in if attempting to introduce the needle in the orifice such attempt fails, it is very possible that the hand holding the apparatus will be injured.

Argentine Pat. No. 239,895, granted to Susana Giron and Hugo Di Placido, on Dec. 29, 1989, protects a device that, as expressed in the description of the invention, "is apt for being located in the access mouthpiece of the residue containers which are used for this type of refuse, in Clinics, Sanatoriums and Hospitals, and consists of a lock", which comprises "an access orifice having its upper part of a larger diameter than the lower one". That is, the needle should be introduced by its point in the larger diameter portion of the orifice and then it should be inserted in the lower portion thereof, and once inserted, the syringe is pulled and then steps are taken to dislodge the needle.

This device is to be located in fixed places and it is not portable, for which reason it is possible that it is not found in the place where it should be used. Then the personnel should have to move for a distance of several metres upto where the device is located, with the risks implied by this fact.

U.S. Pat. No. 4,576,281, owned by University Hospital, granted on Mar. 18, 1986, relates to an apparatus which is stationary, with an orifice in its upper face. Said orifice consists also of a larger diameter portion and another of a lesser diameter, in order to introduce the needle by its point in the wide portion of the cited orifice and then to introduce it in the narrower portion. Then one proceeds to pull the syringe and unlock the needle, which falls in a container. This device is not portable and brings about the same drawbacks of the previous case.

U.S. Pat. No. 4,351,434, owned by Benjamin Elisha, granted on Sept. 28, 1982, protects a device with a container for receiving and holding hypodermic needles. The container has an opening through which a discardable needle having a needle stem and a fitting portion can be passed, while it is mounted in a syringe but which, by withdrawal of the latter, locks the fitting portion of the needle for withdrawing the latter from the syringe.

This device, as that of the U.S. Pat. No. 4,375,849, has the serious drawback that its use has the risk of opposing the point of the needle, which is to be withdrawn, to the hand holding the apparatus, with the very probable chance of wounding said hand in the case of failing in the attempt of introducing the needle through the opening of the device.

Within the state of the art, U.S. Pat. Nos. 4,793,587, granted to Willoughby G. M., and 4,738,362 granted to Beral Enterprises may be cited.

SUMMARY OF THE INVENTION

The object of the present invention does not permit the approach by the hypodermic needle towards the apparatus in a frontal manner by its point. The needle is introduced longitudinally, that is, sideways, rather than end first, reducing in a remarkable manner the possibility of accidents. Also the absolute protection of the hand operating the extracting apparatus is obtained. Another outstanding quality is that said apparatus is portable, and it can be carried inside the pockets of a duster, in the trays for injections carried by nurses, or be left on the tables and then taken from there when an injection has to be applied. Taking into consideration also the potential risks run by persons who are not those habitually manipulating the needles, such as cleanup crews, administrative personnel, waste collecting personnel. etc., the safety offered by the apparatus of the invention is total.

BRIEF DESCRIPTION OF THE DRAWINGS

In order that the present invention be clearly understood and carried into practice, it has been shown in a preferred embodiment in the attached drawings, wherein.

DESCRIPTION OF THE PREFERRED EMBODIMENTS

Figure 1:
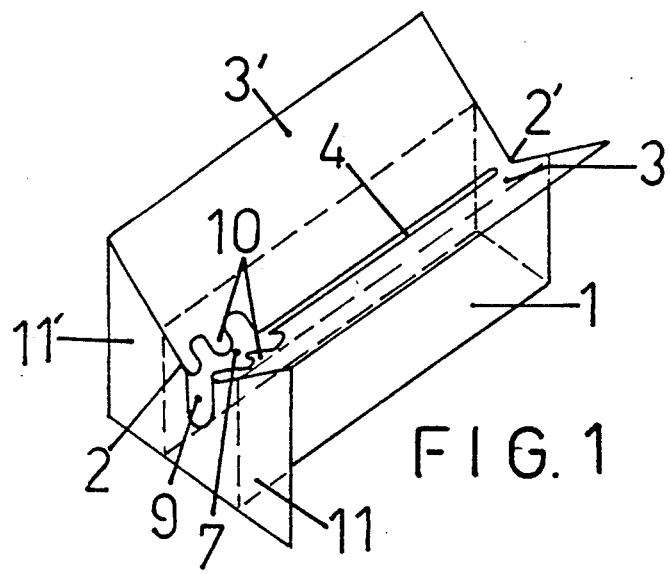
FIG. 1, is a perspective view of the apparatus of the invention.

As shown in FIG. 1, an apparatus in accordance with the present invention constitutes a rigid receptable (1) which is a container of the extracted needles. The receptacle (1) has a longitudinal configuration, horizontally arranged, and open in the upper face. The upper borders of the front and rear ends of said receptacle, are provided with respective notches (2) and (2'), that are V-shaped. The notches are integrally linked one to the other by respective rigid flaps (3) and (3') converging towards the inside of the receptacle, which provide in their converging zone a narrow slot (4), longitudinally extended between said front and rear ends. The slot (4) is capable of permitting the passage of hypodermic needle (5) (see FIG. 2) mounted in a syringe (6), horizontally arranged, towards the inside of the receptacle (1).

Figure 2:
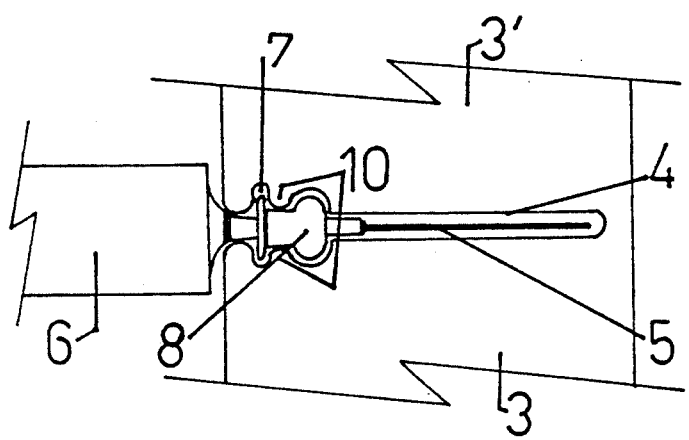
FIG. 2, is an upper plan view of same apparatus, showing the syringe with its respective needle located therein.

The slot (4) has in its front end, an enlargement (7) capable of permitting the passage of an enlarged rear end or cone (8) of the needle (see FIG. 2).

The front end of said receptacle (1) is provided with a second slot (9) projecting downward from the apex of the respective notch (2), said second slot being capable of permitting the introduction of the nozzle of a syringe (6) with the corresponding hypodermic needle (5) arranged therein (see FIG. 2), and permitting the retention and extraction of said needle.

In the enlargement (7) of slot (4), means are provided for preventing the escape or release of the rear end of the hypodermic needle extracted from its seat in the syringe nozzle, constituted by projections (10) in the manner of teeth one in front of the other, which are provided in the facing borders of the enlargement (7).

In the front end of the receptacle (1) associated projections (11) and (11') are provided, frontally extended and integral with the converging rigid flaps (3) and (3'), in the respective ends thereof. Said projections (11) and (11') constitute a protecting means for the user's hand when holding the apparatus during the needle extracting operation.

Figure 6:
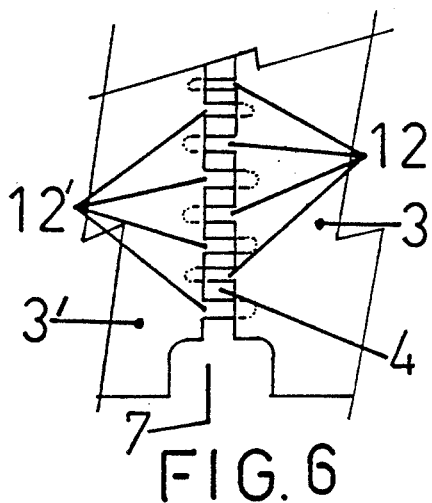
FIG. 6, is a partial upper plan view, of a particular embodiment of the invention illustrated in FIG. 3.
Figure 3:
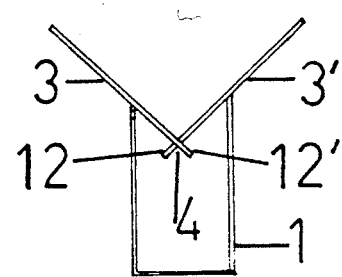

In FIG. 3, a variation of the embodiment of converging flaps (3) and (3') is shown. The narrow slot (4) is provided on both borders and along its entire length from the enlargement (7), with a plurality of projections (12) and (12') in the manner of teeth mutually interlaid, such as it is illustrated in detail in FIG. 6.

Figure 4:
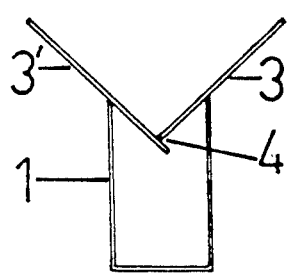
FIGS. 3 through 5, show different constructive embodiments of said apparatus, in cross sections.

In FIG. 4, another variation of the embodiment of the converging flaps (3) and (3') is shown, in which the lower border of one of the flaps (in the case illustrated flap 3') is projected somewhat beyond the convergence zone of both flaps, starting from the enlarged end (7) of the slot (4).

Figure 5:
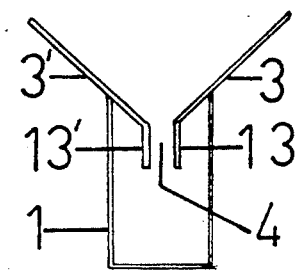

Finally, FIG. 5, represents a third variation of an embodiment of said converging flaps (3) and (3'), in which both flaps project parallel and downward from the enlarged end (7) of the slot (4), providing respective projections (13) and (13'), which form an obtuse angle with the respective flaps (3) and (3').

To operate with the apparatus of this invention the following maneuvers should be executed: 1) The apparatus is held with one hand, between the thumb and the forefinger, keeping the hand protected by the projections (11), (11') that are frontally extended. 2) The hypodermic needle in introduced, along the narrow slot (4), leaving inside the apparatus only said needle, such as it is represented in FIG. 2. 3) In the slot (9) provided in the front face of the receptacle (1), the mounting nozzle of the syringe is introduced. 4) A slight rotating and tractive movement of the syringe is made, with which the disengagement of the needle is produced, the needle falling inside the receptable (1).

It is needed that the dimensions of the receptacle do not allow the needles to rotate inside it, so as to prevent the points of the needles be exposed from the slot (9). Also, the projections (10) in the manner of teeth provided in the enlargement (7), prevent, by any fortuitous movement, the cone of the needles be exposed by said enlargement.

It should be very specially noted that, because the hand is protected by the projections (11), (11'), plus the fact that the introduction of the needle is made, not by means of a frontal attack with the point of the needle, but with the needle longitudinally positioned, the possibility of accident is practically nil.

What is claimed is:

1. A safety apparatus for extracting hypodermic needles from the respective syringe, comprising a rigid receptacle for containing the extracted needles, said receptacle being of longitudinal configuration, horizontally arranged and open at its upper face; the upper edges of the front and rear ends of said receptacle being provided with respective V-shaped notches, integrally linked by respective rigid flaps converging towards the inside of the receptacle, said flaps in their convergence zone forming a narrow slot, longitudinally extended between said front and rear ends, and capable of permitting the passage of a hypodermic needle horizontally arranged to the inside of said receptacle, said slot having in the front end, an enlargement capable of permitting the passage of the enlarged rear end of the needle; the front end of said receptable being provided with a second slot projecting downwardly from the apex of the corresponding notch, said second slot being capable of permitting the introduction of the nozzle of a syringe with the corresponding hypodermic needle arranged therein, and capable of permitting the retention and extraction of said needle; the longitudinally extended slot having in its enlargement, means for preventing the exit to the outside of the rear end of the hypodermic needle extracted from its seat in the syringe nozzle; said front end of the receptacle being further provided with respective projections frontally extended and integral with the converging rigid flaps at the respective front ends of the flaps.

2. A safety apparatus for extracting hypodermic needles from the respective syringe, comprising a rigid receptacle containing the extracted needles, said receptacle being of longitudinal configuration, horizontally arranged and open at its upper face; the upper edges of the front and rear ends of said receptacle being provided with respective V-shaped notches, integrally linked by respective rigid flaps converging towards the inside of the receptacle, said flaps in their converging zone forming a narrow slot, longitudinally extended between said front and rear ends and capable of permitting the passage of a hypodermic needle horizontally arranged to the inside of said receptacle, the lower edge of one of said converging rigid flaps projecting slightly beyond said converging zone of both flaps, an enlargement being provided in the front end of said slot, said enlargement being capable of permitting the passage of the rear enlarged end of the needle; the front end of said receptacle being provided with a second slot projecting downwardly from the apex of the corresponding notch, said second slot being capable of permitting the introduction of the nozzle of a syringe with the respective hypodermic needle arranged therein, and capable of permitting the retention and extraction of said needle; the longitudinally extending slot having in its enlargement, means for preventing the exit to the outside of the rear end of the hypodermic needle extracted from its seat in the syringe nozzle, said front end of the receptacle being further provided with corresponding projections frontally extended and integral with the converging rigid flaps at the respective front ends of the flaps.

3. A safety apparatus for extracting hypodermic needles from the respective syringe, comprising a rigid receptacle containing the extracted needles, said receptacle being of longitudinal configuration, horizontally arranged and open at its upper face, the upper edges of the front and rear ends of said receptacle being provided with respective V-shaped notches, integrally linked by respective rigid flaps converging towards the inside of the receptacle, said flaps in their converging zone forming a narrow slot, longitudinally extended between said front and rear ends, and capable of permitting the passage of a hypodermic needle horizontally arranged to the inside of said receptacle; the lower edges of the converging rigid flaps being parallel and downwardly projected, said lower edges forming an obtuse angle with the respective flaps, an enlargement being provided in the front end of said slot, said enlargement being capable of permitting the passage of the enlarged rear end of the needle; the front end of said receptacle being provided with a second slot projecting downwardly from the apex of the corresponding notch, said second slot being capable of permitting the introduction of the syringe nozzle with the respective hypodermic needle arranged therein, and capable of permitting the retention and extraction of said needle; the longitudinally extended slot having in its enlargement, means for preventing the exit to the outside of the rear end of the hypodermic needle extracted from its seat in the syringe nozzle; said front end of the receptacle being further provided of corresponding projections frontally extending and integral with the converging rigid flaps at the respective front ends of the flaps.

4. A safety apparatus for extracting hypodermic needles from the respective syringe comprising a rigid receptacle for containing the extracted needles, said receptacle being of a longitudinal configuration horizontally arranged and open at its upper face; the upper edges of the front and rear ends of said receptacle being provided with respective V-shaped notches, integrally linked by corresponding rigid flaps converging to the inside of the receptacle, said flaps in their converging zone forming a narrow slot, longitudinally extended between said front and rear ends, and capable of permitting the passage of a hypodermic needle, horizontally arranged to the inside of said receptacle; said slot being provided with projections in the manner of teeth interleaved one with the other on both borders and in all the slot length, from an enlargement provided in the front end of said slot, said enlargement being capable of permitting the passage of the enlarged rear end of the needle; the front end of said receptacle being provided with a second slot projecting downwardly from the apex of the respective notch, said second slot being capable of permitting the introduction of the nozzle of a syringe with the corresponding hypodermic needle arranged therein, and capable of permitting retention and extraction of said needle; the slot longitudinally extended in its enlargement having means for preventing the exit outside of the rear end of the hypodermic needle extracted from its seat in the syringe nozzle; said front end of the receptacle being also provided with corresponding projections frontally extended and integral with the converging rigid flaps at the respective front ends of the flaps.

5. A safety apparatus for extracting hypodermic needles from the respective syringe comprising a rigid receptacle for containing the extracted needles, said receptacle being longitudinally configurated, horizontally arranged and open at its upper face; the upper edges of the front and rear ends of said receptacles being provided with respective V-shaped notches, integrally linked by corresponding rigid flaps converging to the inside of the receptacle, said flaps in their converging zone forming a narrow slot, longitudinally extended between said front and rear ends, and capable of permitting the passage of a hypodermic needle horizontally arranged to the inside of said receptacle, said slot having in its front end, an enlargement capable of permitting the passage of the enlarged rear end of the needle; the front end of said receptacle being provided with a second slot projecting downwardly from the apex of the respective notch and capable of permitting the introduction of the nozzle of a syringe with the corresponding hypodermic needle arranged therein, and the retention and extraction of said needle; the longitudinally extended slot having its enlargement, means for preventing the exit to outside of the rear end of the hypodermic needle extracted from its seat in the nozzle of the syringe, said means including projections in the manner of teeth one facing the other, provided in the facing borders of said enlargement; said front end of the receptacle being also provided with corresponding projections frontally extended and integral with the converging rigid flaps at the respective front ends of the flaps.

6. A safety apparatus for extracting hypodermic needles from the respective syringe, comprising a rigid receptacle for containing the extracted needles, said receptacle being of longitudinal configuration, horizontally arranged and open at its upper face; the upper borders of the front and rear ends of said receptacle being provided with respective V-shaped notches, integrally linked by corresponding rigid flaps converging to the inside of the receptacle, said flaps in their converging zone forming a narrow slot, longitudinally extended between said front and rear ends, capable of permitting the passage of a hypodermic needle horizontally arranged to the inside of said receptacle, the lower border of one of said converging rigid flaps projecting slightly beyond said converging zone of both flaps, from an enlargement provided in the front end of said slot, said enlargement being capable of permitting the passage of the rear end of the needle; the front end of said receptacle being provided with a second slot projecting downwardly from the apex of the respective notch, and capable of permitting the introduction of the nozzle of a syringe with the corresponding hypodermic needle arranged therein, and capable of permitting retention and extraction of said needle, the longitudinally extended slot having in its enlargement means for preventing the exit to the outside of the rear end of the hypodermic needle extracted from its seat in the nozzle of the syringe, said means for preventing including projections in the manner of teeth one in front of the other, provided in the facing borders of said enlargement; said front end being further provided with corresponding projections frontally extended and integral with the converging rigid flaps at the respective front ends thereof.

7. A safety apparatus for extracting hypodermic needles from the respective syringe, comprising a rigid receptacle for containing the extracted needles, said receptacle being of longitudinal configuration, horizontally arranged and open at its upper face; the upper edges of the front and rear ends of said receptacle being provided with respective V-shaped notches, integrally linked by corresponding rigid flaps converging to the inside of the receptacle, said flaps in their converging zone forming a narrow slot, longitudinally extended between said front and rear ends, capable of permitting the passage of a hypodermic needle horizontally arranged to the inside of said receptacle; the lower edges of the converging rigid flaps being projected parallel and downwardly and said projected lower edges forming an obtuse angle with the respective flaps, an enlargement provided in the front end of said slot, being capable of permitting the passage of the enlarged rear end of the needle; the front end of said receptacle being provided with a second slot projecting downwardly from the apex of the respective notch, said second slot being capable of permitting the introduction of the nozzle of a syringe with the respective hypodermic needle arranged therein, and capable of permitting the retention and extraction of said needle; the longitudinally extended slot having in its enlargement, means for preventing the exit outside of the rear end of the hypodermic needle extracted from its seat in the nozzle of the syringe, said means being constituted by projections in the manner of teeth one facing the other, provided in the facing borders of said enlargement; said front end of the receptacle being further provided with corresponding projections frontally extended and integral with the converging rigid flaps at the respective front ends thereof.

8. A safety apparatus for extracting hypodermic needles from the respective syringe, comprising a rigid receptacle for containing the extracted needles, said receptacle being of longitudinal configuration, horizontally arranged and open in its upper face; the upper edges of the front and rear ends of said receptacles being provided with respective V-shaped notches, integrally linked by corresponding rigid flaps converging to the inside of the receptacle, said flaps in the converging zone forming a narrow slot, longitudinally, extended between said front and rear ends, capable of permitting the passage of a hypodermic needle horizontally arranged to the inside of said receptacle; said slot being provided with projections in the manner of teeth interleaved one with the other on both borders and in all the slot length, from an enlargement provided in the front end of said slot, said enlargement being capable of permitting the passage of the enlarged rear end of the needle; the front end of said receptacle being provided with a second slot projecting downwardly from the apex of a respective notch' and capable of permitting the introduction of the nozzle of a syringe with the respective hypodermic needle arranged therein, and the retention and extraction of said needle; the longitudinally extended slot having in its enlargement, means for preventing the exit to outside of the rear end of the hypodermic needle extracted from its seat in the nozzle of the syringe, said preventing means being projections in the manner of teeth one facing the other, provided on the facing borders of said enlargement; said front end of the receptacle being provided with corresponding projections extended frontally, and integral with the converging rigid flaps, in the respective ends thereof.

* * * * *